Figure 1:
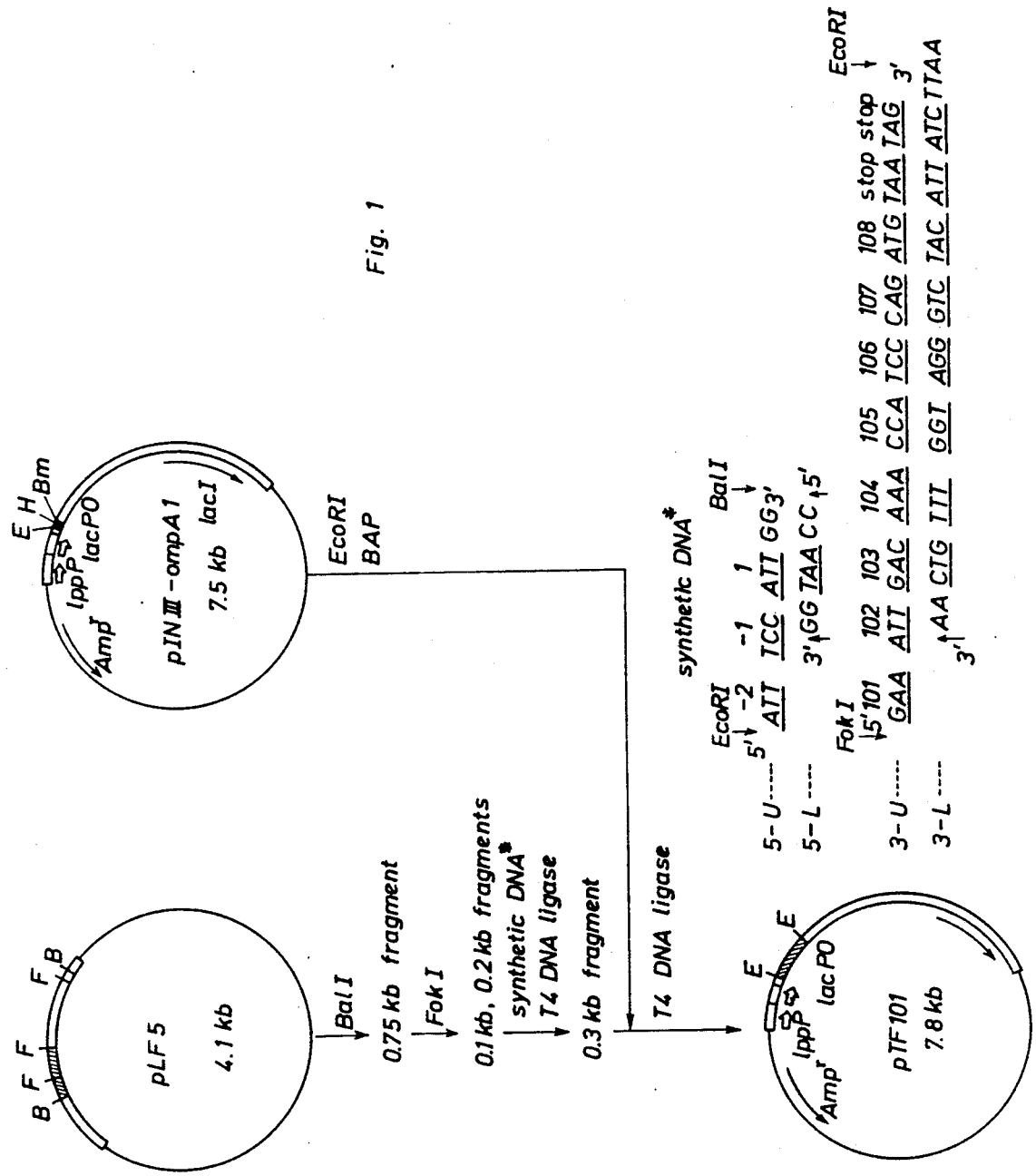

United States Patent [19]
Kimizuka et al.

[11] Patent Number: 5,049,658
[45] Date of Patent: Sep. 17, 1991

[54] POLYPEPTIDE WITH CELL-SPREADING ACTIVITY

[75] Inventors: Fusao Kimizuka, Ohmihachiman; Tatsuru Kinoshita, Kyoto; Yoh'ichi Ohdate, Amagasaki; Yuki Sugahara, Otsu; Ikunoshin Kato, Uji, all of Japan

[73] Assignee: Takara Shuzo Co., Ltd., Kyoto, Japan

[21] Appl. No.: 291,894

[22] Filed: Dec. 29, 1988

[30] Foreign Application Priority Data

Jan. 5, 1988 [JP] Japan ................................. 63-148

[51] Int. Cl.$^5$ ............................................ C07K 13/00
[52] U.S. Cl. ................................................. 530/350
[58] Field of Search ................................ 530/350, 382

[56] References Cited
PUBLICATIONS

Hayashi et al., J. of Biol. Chem. 258(5) 3332–3340 (1983).
Silnitzer e tal., In Vitro Cellular & Div. Biol. 21(1) 73–78 (1985).

Primary Examiner—Margaret Moskowitz
Assistant Examiner—Shelly J. Guest
Attorney, Agent, or Firm—Armstrong, Nikaido, Marmelstein, Kubovcik & Murray

[57] ABSTRACT

A polypeptide having the cell-spreading activity of human fibronectin. Methods of preparing the polypeptide are described.

1 Claim, 5 Drawing Sheets

POLYPEPTIDE WITH CELL-SPREADING ACTIVITY

This invention relates to a protein which has cell-spreading activity like that of fibronectin. More particularly, the invention relates to a polypeptide which has the cell-spreading activity of fibronectin of human origin; and also to a method for the preparation of said polypeptide.

Fibronectin is a multifunctional glycoprotein which is widely distributed in a variety of animal tissues and body fluids and also on the surface of cultured cells and elsewhere. This compound has various physiological effects, such as causing attachment, spreading, migration, differentiation, proliferation, and phagocytosis by cells, among others. This glycoprotein participates in such activities as tissue reconstruction, tissue construction, and protection from infection.

Fibronectin is a polypeptide with a molecular weight of about 250,000 and is a dimer with an S—S bond in the vicinity of the C-terminus. The amino acid sequence of this molecule contains 3 different types of internal repeats, and can be classified as types I, II and III. In addition, there are domain structures which have various functions, with the effect of cell attachment and spreading and the ability to bind to collagen, heparin, fibrin, etc. Of these domains, industrial applications of the biological activity related to the cell attachment and spreading domain have been considered; for example, in the preparation of a coating agent for a substrate for culture, it is possible to use this function in the preparation of a substrate to which cells will bind. Also, this function can be used as an accelerator of cell binding in such preparations as collyrium, lotions, and agents for the healing of wounds. Cell spreading is a phenomenon that follows after cell attachment. For cells to proliferate, with some exceptions, it is necessary for the phenomenon of spreading to take place, not cell attachment alone.

The basic structure which is the minimum essential structure for the cell-attachment domain of fibronectin is the sequence Arg-Gly-Asp-Ser (*Nature*, 309 [1984], 30–33). Japanese Laid-Open Patent (Tokuhyo) 84-501548 discloses a peptide with cell-attachment activity, that is a polypeptide of the molecular weight of 11,500 and that contains this sequence among its sequence with 108 amino acid residues.

However, the cell-attachment activity of this polypeptide with the molecular weight of 11,500 is much weaker than that of fibronectin of natural origin, and it is not necessarily possible to make use of it in the practical applications mentioned above. This difficulty is discussed, for example, in *J. Biol. Chem.*, 260 (1985), 13256–13260. Also, the inventors of this invention have constructed the polypeptide of the molecular weight of 11,500 mentioned above by means of genetic engineering, and compared its cell-spreading activity to that of fibronectin of natural origin with the use of normal rat kidney (NRK) cells. The results were that, whereas fibronectin gave noticeable activity at the dose of 0.1–1 µg/well, the dose of 40 µg/well of the polypeptide with the molecular weight of 11,500 did not have any such activity.

The object of this invention is to identify the amino acid sequence that has substantial cell-spreading activity as the peptide of the cell-spreading domain of fibronectin and to provide a method for producing the same.

Briefly, the present invention relates to a polypeptide wherein the cell-spreading activity is virtually equivalent to that of fibronectin.

The invention also relates to DNA wherein the above mentioned polypeptide is coded.

The present invention further relates to a method for the preparation of the above mentioned polypeptide wherein cells of *Escherichia coli* which have been transformed by a vector that carries the DNA sequence mentioned above is cultured, and the desired polypeptide mentioned above is obtained from the culture broth.

We have conducted a research work wherein there have joined to expression vectors the DNA sequences which code for the polypeptides of various chain lengths corresponding to the cell attachment and spreading domain of fibronectin. After the transformation of host cells, the production of the desired polypeptides, their purification, and the measurement of their cell-spreading activity were conducted.

As the result thereof, we have found that the polypeptide with the molecular weight of 11,500 has almost no cell-spreading activity, but that the polypeptide consisting of the 283 amino acids toward the N-terminus of that polypeptide has almost the same cell-spreading activity as that of fibronectin of natural origin. This invention is based upon this finding.

The complete amino acid sequence of fibronectin of human origin and its cDNA sequence were published in 4 (1985), 1755–1759. The steps by which The *EMBO Journal*, 4 (1985), 1755–1759. The steps by which the cDNA corresponding to the amino acid sequence of the cell attachment and spreading domain of fibronectin can be cloned are well known. For example, an RNA fraction containing poly(A) from the liver is prepared, and a cDNA library can be prepared by such method as the OkayamaBerg method or the Gubler-Hoffmann method. Alternatively, such cDNA libraries are commercially available. Thus it is possible to obtain them from, for example, the Clontech Laboratories, Inc. As a method to obtain the desired cDNA clone from the cDNA library, the DNA which corresponds to the amino acid sequence can be used as a probe with the techniques of colony hybridization or plaque hybridization. The clones which hybrized with the probe are selected, and DNA is extracted from the cell pellet or a phage lytic solution and cleaved with restriction enzymes. Insertions are confirmed by the use of electrophoresis. When necessary, Southern blotting is used to check the insert being hybridized with the probe. In the final step, by the study of the base sequence of the insert by the dideoxy method or the like, the identity of the desired clone can be checked.

When necessary, the vector which carried the cDNA coding for the cell-spreading domain of fibronectin can be amplified in the host cells, purified, and cleaved with restriction enzymes so that the cDNA portion can be removed; electrophoresis can be used to purify the cDNA fragments. These cDNA fragments are joined by use of a DNA ligase by inframe ligation to expression vectors, and by their introduction to host cells, it is possible to express the cDNA. Any of the known vectors can be used as expression vectors for *Escherichia coli* as the host, but for preference, a host-vector system which can have its expression induced and which has strong promoter activity is used. As such vectors, there are, for example, the vector which carries the λPL promoter, the vector which carried the lac promoter, the vector which carries the trp promoter, the vector which carries the pst promoter, the vector which carries both the lac and the trp promoters, the vector which carries the lpp promoter, the vector which carries both the lpp and lac promoters, and other such known vectors (refer to Yoshiyuki Sakai, "Vector DNA", Kodansha Scientific, 1986).

Also, it is possible to use vectors in which exogenous genes can be inserted downstream from a gene for a signal peptide so that the peptide which has been expressed can be secreted.

When a peptide is expressed by the gene for the desired peptide by the use of an expression vector which can be joined downstream from a gene for a signal peptide or by the use of an expression vector directly, by the joining of the vector, sometimes a certain length of the amino acid sequence of vector origin are connected to the N-terminus of the desired peptide. By the addition of this sequence, there is caused no essential change in the cellspreading activity of the polypeptide, and it is possible to use the polypeptide as is. However, it is possible, whenever necessary, to remove this sequence by the techniques of gene engineering. This removal involves what is called site-specific mutagenesis, which is a well-established technique.

Generally, when the foreign peptides are expressed in *Escherichia coli,* they hinder the growth of the host cells. So, the cells are grown in the presence of a repressor of the promoter; then, the inactivation of the repressor or the addition of an inducer will cause the induction of the expression of the foreign peptide. When the foreign peptide does not interfere with the growth of the host cells of *Escherichia coli,* the use of this technique is unnecessary. The polypeptide expressed in this invention does not inhibit the host cells of *Escherichia coli,* and there is no need to limit the induction of its expression.

The vector carrying the gene for the cell-spreading polypeptide can be used to transform *Escherichia coli* by the usual methods, and these transformant cells may be cultured under conditions suitable for the expression of the polypeptide, whereby the desired polypeptide can be expressed. For confirmation whether the desired polypeptide is being expressed, immunoblotting can be used. For example, buffer which contains SDS is added to the cells and the whole is heated, by which the total protein is made soluble and after this, polyacrylamide gel electrophoresis is conducted. After the electrophoresis pattern is transferred to a nitrocellulose or a nylon membrane. The membrane is allowed to incubate first with a monoclonal antibody specific for the cell-spreading domain of fibronectin, and then with an enzyme-labelled second antibody. The enzyme activity of the second antibody so bound gives rise to color in a chromogenic substrate, and thus it is possible to verify the presence of the band for the desired polypeptide.

The cell-spreading polypeptide can be purified from cells of *Escherichia coli* by, for example, the following method. A cell pellet of harvested cells is suspended in buffer, and ultrasonication is applied to give a soluble fraction and an insoluble fraction. The latter is solubilized in a buffer which contains 7 M urea. The soluble fractions are collected, and placed on a Sepharose 4B column bound with the same antibody as that used for immunoblotting, so that purification is effected by affinity binding. As the eluent, buffer in the vicinity of pH 2 is used. By immunoblotting, the fraction with the desired polypeptide is collected, and it is possible to obtain an almost pure polypeptide judged by electrophoresis. When necessary, purification can be further conducted with FPLC (Pharmacia) or HPLC. The polypeptide obtained in this way can be investigated for the presence or absence of cell-spreading activity in, for example, the following way. A buffer in which a sample has been dissolved is made to adsorb onto wells of a microtiter plate, after which a suspension of normal rat kidney (NRK) cells is added, and the plate incubated for 1 hour at 37° C. Then the morphological changes in the cells are observed in order to determine the presence or absence of cell-spreading activity. By the comparison of the minimum dose needed for spreading activity to occur in each well with the activity of fibronectin, it is possible to evaluate the strength of the spreading activity.

In this way, a number of polypeptides which correspond to the cell-spreading domain of fibronectin were produced by genetic engineering, and their biological activities were studied, thereby it was possible to identify the polypeptide sequence which is necessary and sufficient for the expression of spreading activity. Table 1 to be indicated later shows a comparison of the cell-spreading activity of the polypeptides thus obtained with that of fibronectin. These results show that polypeptides which contain Ala $^{1235}$-Met$^{1517}$ have cell-spreading activity which is almost the same strength as that of fibronectin. The polypeptide with cell-spreading activity can be used as such or as bound to other peptides via a bifunctional crosslinker. As methods that can be used for the binding with other peptides, there are, for example, the addition of a cystein residue to the C-terminus of the peptide, and the introduction of a crosslinker, for example, 3-(2-pyridyldithio)propionic acid-N-hydrozysuccinimide ester, and the binding with the amino group of another peptide. It is easy to add a cystein residue to the C-terminus of a peptide by use of genetic engineering; for example, when the gene which codes for the desired polypeptide is cloned, synthetic DNA can be used to replace the codon that corresponds to the cystein at the 3' terminus.

Examples of the polypeptides of this invention will be listed below.

Thus the polypeptides are those which contain at least the amino acid sequence shown by the following general formula I:

[I]

Ala Val Pro Pro Pro Thr Asp Leu Arg Phe Thr Asn Ile Gly Pro
Asp Thr Met Arg Val Thr Trp Ala Pro Pro Pro Ser Ile Asp Leu
Thr Asn Phe Leu Val Arg Tyr Ser Pro Val Lys Asn Glu Glu Asp
Val Ala Glu Leu Ser Ile Ser Pro Ser Asp Asn Ala Val Val Leu
Thr Asn Leu Leu Pro Gly Thr Glu Tyr Val Val Ser Val Ser Ser
Val Tyr Glu Gln His Glu Ser Thr Pro Leu Arg Gly Arg Gln Lys
Thr Gly Leu Asp Ser Pro Thr Gly Ile Asp Phe Ser Asp Ile Thr
Ala Asn Ser Phe Thr Val His Trp Ile Ala Pro Arg Ala Thr Ile
Thr Gly Tyr Arg Ile Arg His His Pro Glu His Phe Ser Gly Arg
Pro Arg Glu Asp Arg Val Pro His Ser Arg Asn Ser Ile Thr Leu
Thr Asn Leu Thr Pro Gly Thr Glu Tyr Val Val Ser Ile Val Ala
Leu Asn Gly Arg Glu Glu Ser Pro Leu Leu Ile Gly Gln Gln Ser
Thr Val Ser Asp Val Pro Arg Asp Leu Glu Val Val Ala Ala Thr
Pro Thr Ser Leu Leu Ile Ser Trp Asp Ala Pro Ala Val Thr Val
Arg Tyr Tyr Arg Ile Thr Tyr Gly Glu Thr Gly Gly Asn Ser Pro
Val Gln Glu Phe Thr Val Pro Gly Ser Lys Ser Thr Ala Thr Ile
Ser Gly Leu Lys Pro Gly Val Asp Tyr Thr Ile Thr Val Tyr Ala
Val Thr Gly Arg Gly Asp Ser Pro Ala Ser Ser Lys Pro Ile Ser
Ile Asn Tyr Arg Thr Glu Ile Asp Lys Pro Ser Gln Met

Also, included in this invention are those to which a cystein residue has been added to the C-terminus of the amino acid sequence shown above in general formula I.

Figure 2:
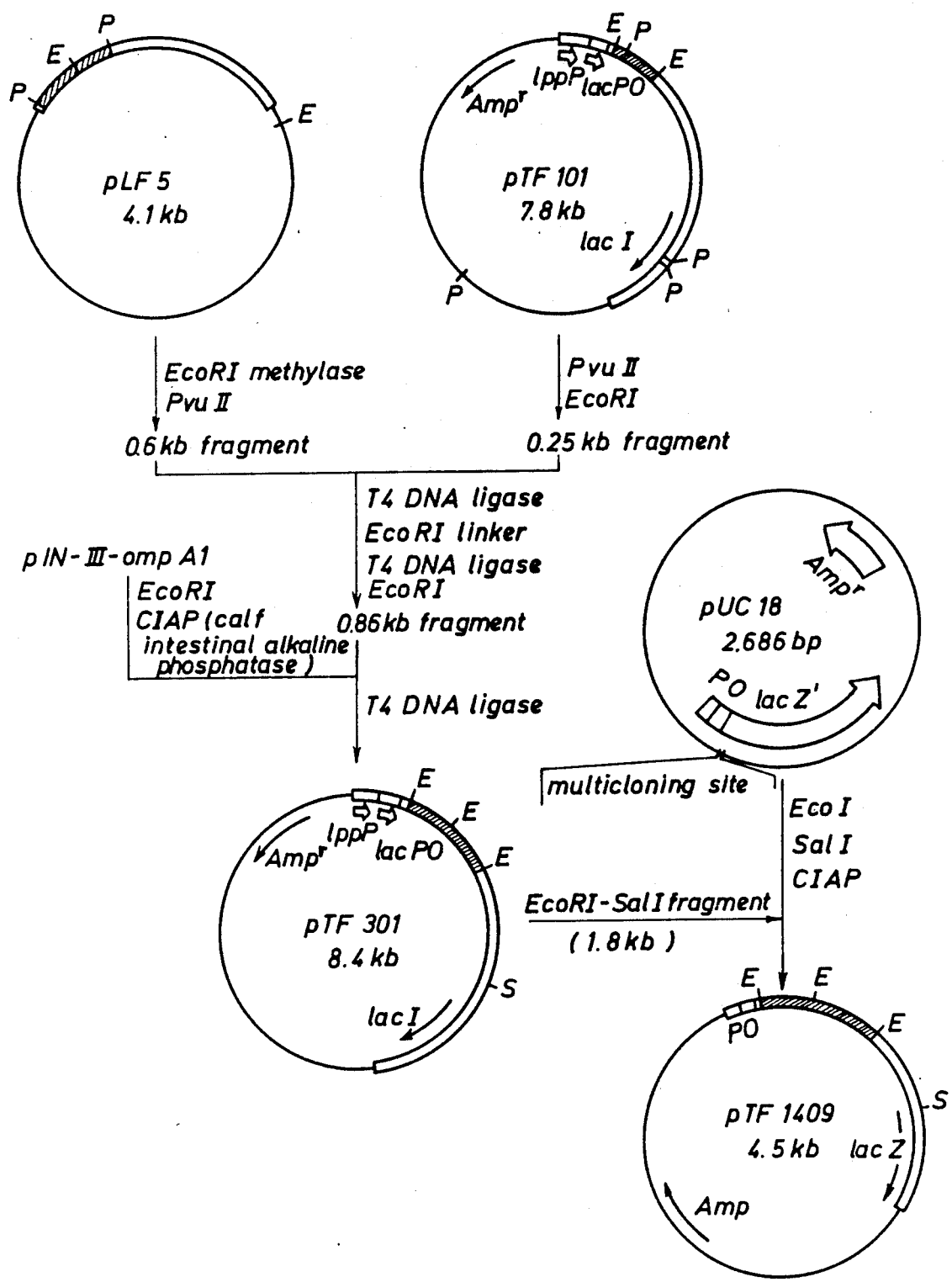
Figure 3:
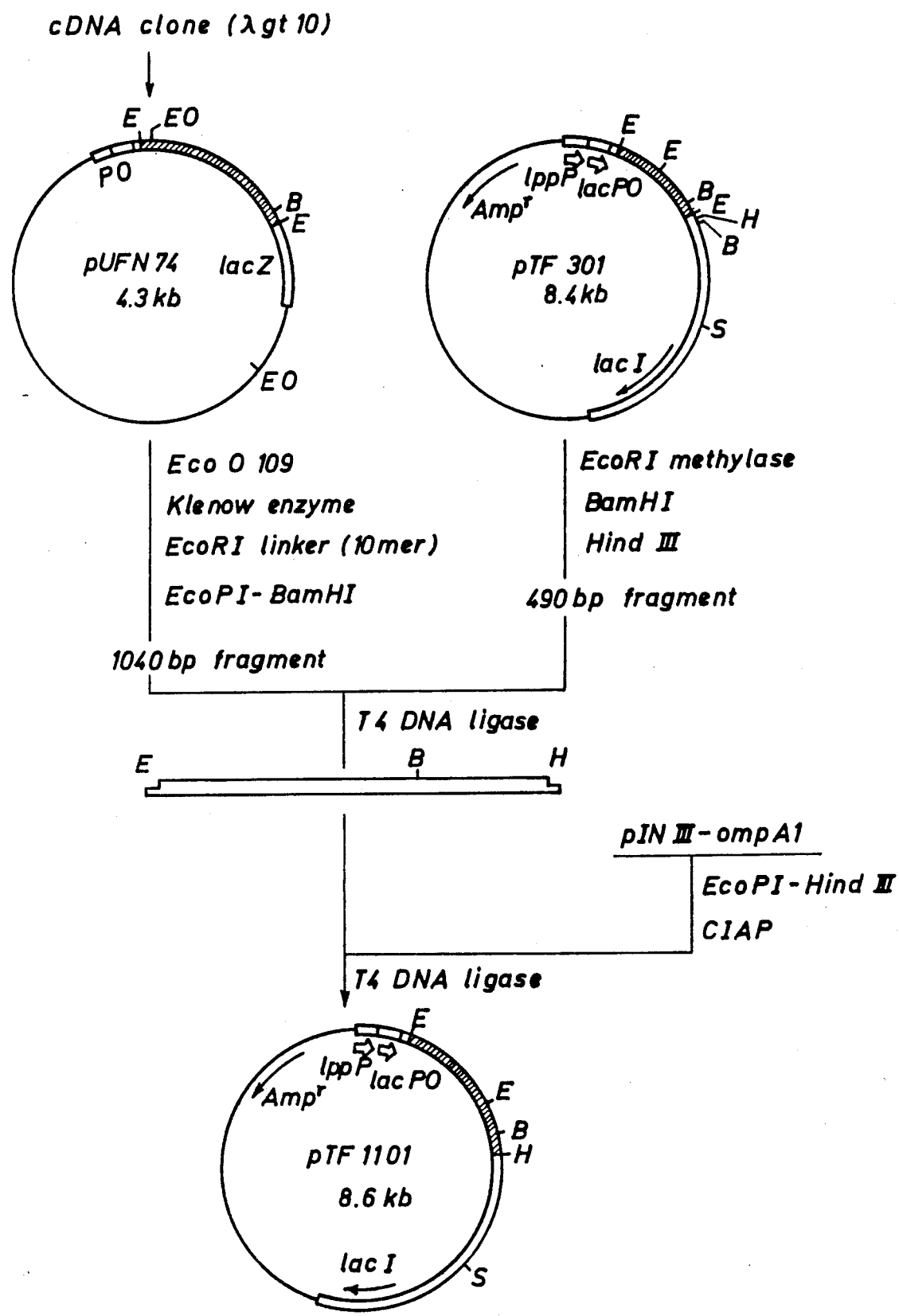
Figures 1, 4:
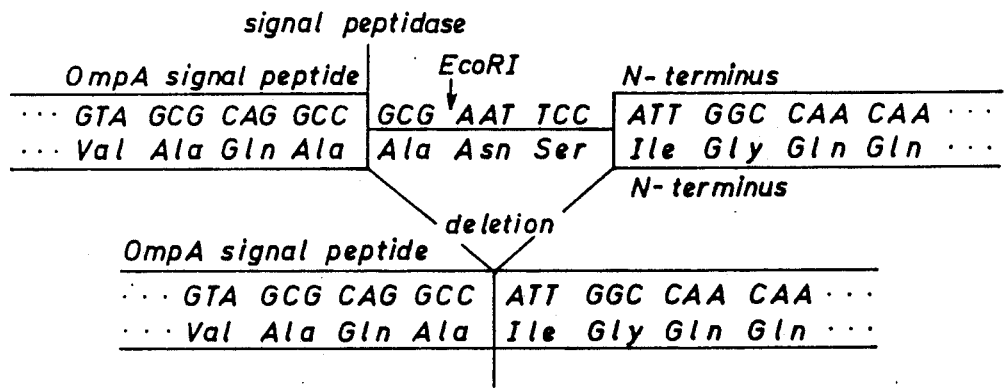
Figures 2, 4:
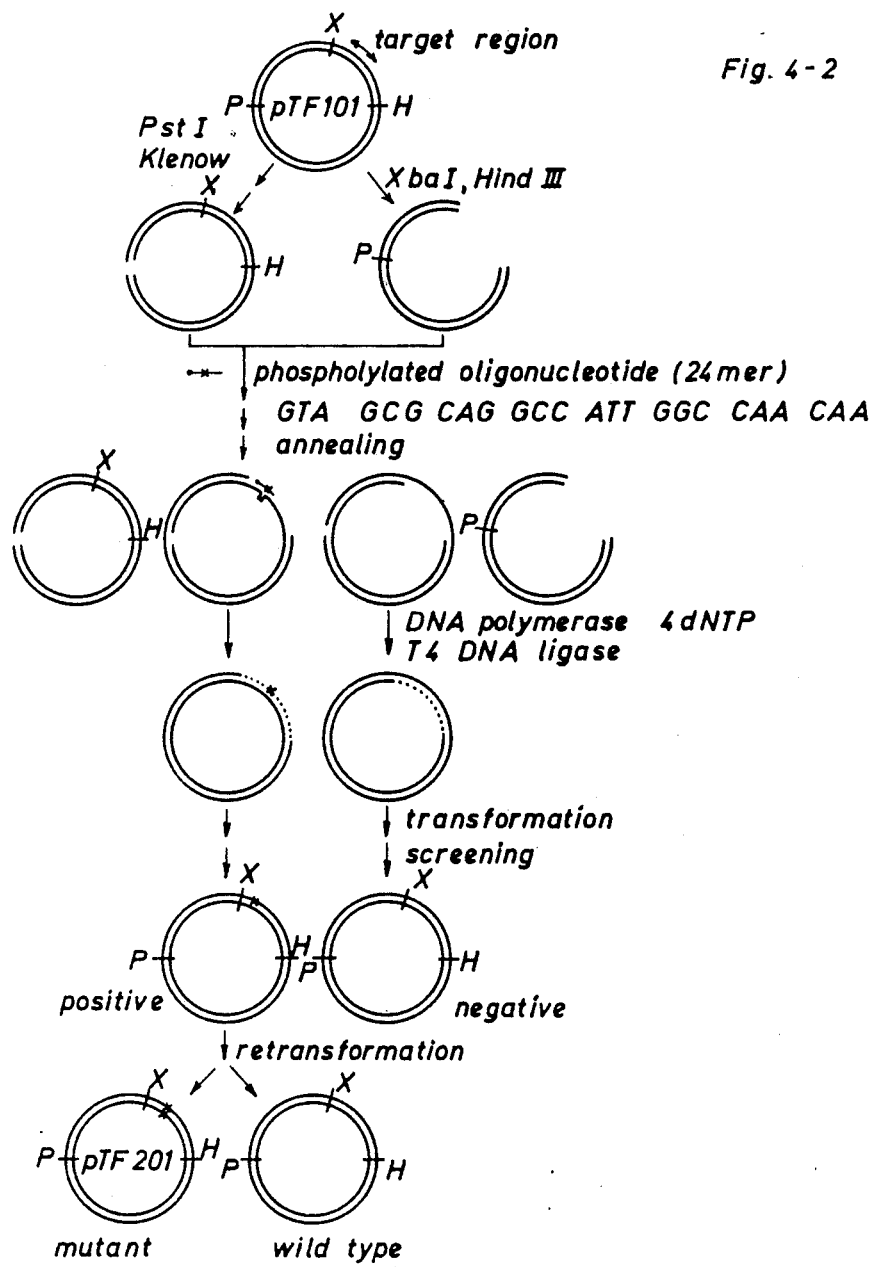
Figure 5:
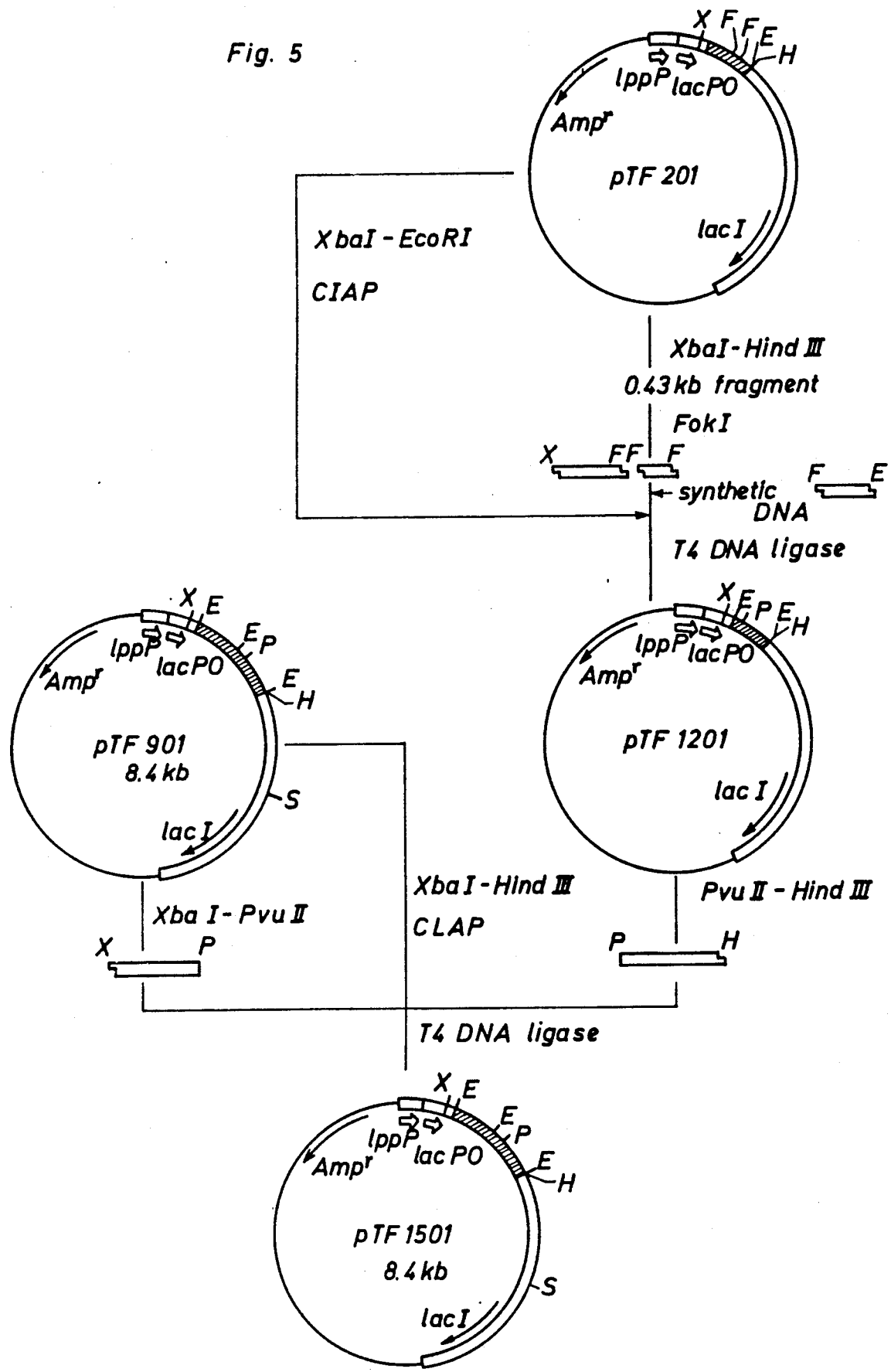

The invention will be further explained in more detail by the following Examples, which partly refer to the accompanying drawings wherein;

FIG. 1 is a diagram of the processes involved in the construction of an expression plasmid which carries the DNA sequence which codes for the polypeptide including the Ile$^{1410}$-Met$^{1517}$ sequence of fibronectin, FIG. 2 is a diagram of the processes in the construction of an expression plasmid which carries the DNA sequence which codes for the polypeptide including the Ala$^{1235}$-Met$^{1517}$ sequence of fibronectin, FIG. 3 is a diagram of the processes involved in the construction of an expression plasmid which carries the DNA sequence which codes for the polypeptide including the
Gly$^{1014}$-Met$^{1517}$ sequence of fibronectin, FIG. 4-1 is a diagram showing the DNA sequence of pTF101 and the amino acid sequence both before and after removal of the extra sequence, FIG. 4-2 is a diagram of the processes involved in the removal of the extra DNA sequence from pTF101 by the use of site-specific mutagenesis, and FIG. 5 is a diagram of the process involved in the construction of an expression plasmid which carries the DNA sequence which codes for a polypeptide with a cystein residue attached to the C-terminus.

EXAMPLE 1

Cloning of the cDNA fragment which codes for Ile$^{1410}$-Met$^{1517}$ (108 amino acid residues) of fibronectin (see FIG. 1):

FIG. 1 is a diagram of the processes involved in the construction of an expression plasmid which carries the DNA sequence which codes for the polypeptide including
the Ile$^{1410}$-Met$^{1517}$ sequence of fibronectin. (1-1) Preparation of cDNA fragments:

First, 100 μg of a plasmid, pLF5 (reported in *Biochemistry*, 25 [1986], 4936–4941) which is of 4.1 kilobases and which contains the cDNA sequence which codes for the cell-spreading domain of fibronectin was put into 200 μl of a reaction mixture containing a buffer for use with the restriction enzyme e,uns/BalI and 100 units of BalI, and the mixture was incubated for 2 hours at 37° C. The reaction mixture was then put on an HPLC column of DEAE-4000 (6×125 mm; Nucleogen) and eluted with a concentration gradient of KCl in a 30 mM potassium phosphate buffer (pH 6.5) which contains 5 M urea, and precipitated with isopropyl alcohol, which gave 7.5 μg of 0.75 kb fragments. Next, these fragments were treated with 30 units of FokI for 1 hour at 37° C., and by the same purification method, 60 ng of 92-bp fragments and 140 ng of 203-bp fragments were obtained.

(1-2) Preparation of synthetic DNA linker

So that the cDNA fragments could be joined to a vector, 5'-end and 3'-end linkers were chemically synthesized by the following method. The base sequence is shown in FIG. 1. The upper strand of the 5'-end linker (chain length, 11), labelled 5 U, the lower strand of the 5'-end linker (chain length, 7), labelled 5 L, the upper strand of the 3'-end liner (chain length, 30), labelled 3 U, and the lower strand of the 3'-end linker (chain length, 30), labelled 3 L, were synthesized by use of the DNA synthesizer of Applied Biosystems, Inc. After deprotection, 5 U and 5 L were purified by ion-exchange HPLC on a TSK gel DEAE-2000 column, and desalted on SepPak (Waters), giving 60 μg and 40 μg, respectively. 3 U and 3 L were separated by 12% polyacrylamide gel electrophoresis which contains 7 M urea, and after they were removed from the gel, they were desalted in the same way as for the 5 U and 5 L, giving 32 μg and 26 μg, respectively. The base sequences were checked by the solid-phase MaxamGilbert method. Each strand was then phosphorylated on its 5' terminus in the following way. First, 25 μg of DNA was dissolved in 10 μl of distilled water, and put into 20 μl of a solution of buffer for use with polynucleotide inase (PNK) containing 50 mM Tris-HCl, pH 7.6, 10 mM MgCl$_2$, and 10 mM DTT, 1 mM ATP, and 5 units of PNK; the mixture was incubated for 1 hour at 37° C.; then the reaction was stopped by heat treatment at 65° C. for 10 minutes. After the phosphorylation, by the annealing of 5 U with 5 L and of 3 U with 3 L, the strands were made double-stranded. That is, equal amounts of 5 U and 5 L were mixed together, and left at 60° C. for 10 minutes, after which the mixture was allowed to cool to room temperature gradually, and then cooled further to 15° C. The 3 U and 3 L were treated in the same way.

(1-3) Binding of cDNA fragments and the linkers

The two kinds of linkers prepared in section (1-2) above and the two kinds of DNA fragments (with 92 bp and with 203 bp) prepared in section (1-1) above were used, and ligated together. For this, 0.5 pmol of each kind of cDNA fragment and 5 pmol of each kind of linker were put into 20 μl of a solution containing a ligation buffer [66 mM Tris-HCl, pH 7.6, and 6.6 mM MgCl$_2$] and also 0.5 mM ATP, 10 mM DTT, and 2.8 units of T4 DNA ligase, at 16° C.; the mixture was incubated overnight. The reaction mixture was heated for 10 minutes at 65° C., and then two volumes of cold ethanol was added, and the whole left at −70° C. for 30 minutes. After this, the precipitated DNA was collected by centrifugation. This DNA was put into 20 μl of a reaction mixture made of buffer for use with EcoRI and 7.5 units of EcoRI, and incubated for 30 minutes at 37° C. Then the mixture was subjected to polyacrylamide electrophoresis, thereby 336-bp fragments were obtained. These were extracted for 10 hours at 37° C. in a gel elution buffer (0.5 M ammonium acetate, 0.01 M magnesium acetate, and 1 mM EDTA), after which the fragments were precipitated with ethanol, and the DNA was collected. This DNA was dissolved in 20 μl of TE (10 mM Tris-HCl and 1 mM EDTA, pH 8.0).

(1-4) Binding of cDNA fragments bound with linkers to a vector

First, 1 μg of the secretion-expression vector pIN-III-ompA-1 (reported in the *EMBO Journal*, 3 [1984], 2437–2442) was incubated together with 5 units of EcoRI in buffer for use with EcoRI for 1 hour at 37° C., and next, 0.5 unit of alkaline phosphatase was added; and incubation continued for another hour. The reaction mixture was treated twice with phenol, and ethanol precipitation was used to give 0.5 μg of DNA. This DNA was cleaved with EcoRI, and then 0.1 μg of dephosphorylated pIN-III-ompA-1 vector was put into a mixture with 0.1 μg of the DNA fragments obtained in section (1-3) above together with 10 μl of buffer for use with T4 DNA ligase, 0.5 mM ATP, 10 mM DTT, and 1.8 units of T4 DNA ligase, in a total volume for the reaction mixture of 30 μl. This mixture was incubated overnight at 16° C. Then 15 μl of this reaction mixture was used in the transformation of *Escherichia coli* cells.

(1-5) Transformation of cells of *Escherichia coli*

Cells of *Escherichia coli* SB221 (The *EMBO Journal*, 3 [1984], 2437-2442) were put into a 20 ml test tube containing 5 ml of L-broth (Bactotrypton, 10 g/l; yeast extract, 5 g/l; NaCl, 5 g/l; pH 7.2) and cultured overnight with agitation at 37° C. Then 0.05 ml of this culture broth was used to inoculate 5 ml of fresh L-broth, and culture was continued with agitation until the absorbance at 600 nm reached 0.6. This culture broth was cooled over ice and centrifuged for 5 minutes at 5000 rpm at 4° C. The supernatant was removed. This was mixed with 2.5 ml of an ice-cold 0.1 M $MgCl_2$ solution, after which it was centrifuged in the same way and the supernatant removed. This was mixed with 1.25 ml of ice-cold 0.1 M $CaCl_2$, immediately mixed with ice-water, and left for 30 minutes. The mixture was centrifuged and the supernatant removed; then it was mixed with 0.1 ml of ice-cold 0.1 M $CaCl_2$ to suspend it rapidly. The suspension was mixed with 10 μl of the reaction mixture obtained in section (1-4) above, and left for 30 minutes in an ice bath. Next, it was heated to 42° C. for 2 minutes. Then, 1 ml of L-broth heated to 37° C. was added, and the whole was incubated for 30 minutes at 37° C. After this, the mixture was cultured for 1 hour at 37° C. with agitation. The culture broth was spread on L agar medium that contained 50 μg/ml ampicillin, and colonies which grew after overnight culture at 37° C. were isolated. About 200 colonies were obtained, and fourteen of these were analyzed for plasmids.

(1-6) Analysis of plasmids

After 14 transformants were cultured with agitation overnight in 1.5 ml of L-broth containing 50 μg/ml ampicillin, the cultures were centrifuged and the cell pellets were obtained. The cell pellets were suspended in 100 μl of solution A (50 mM glucose, 10 mM EDTA, 25 mM Tris-HCl, pH 8.0, and 2 mg/ml lysozyme), and left at room temperature for 5 minutes. Then 200 μl of solution B (0.2 N NaOH and 1 % SDS) was added to the suspension, and the container was rapidly inverted five times and then left at 0° C. for 10 minutes. To the container, 150 μl of 5 M potassium acetate (pH 5.0) was added, followed by the addition of two volumes of cold ethanol, and the mixture was left at −70° C. for 30 minutes, after which it was centrifuged and the DNA was obtained. The DNA was washed with 80% ethanol, and the ethanol and water were removed under reduced pressure. The residue was dissolved in a small amount of TE. One portion of the solution (0.1 μg) was allowed to react for 1 hour at 37° C. in 10 μl of a reaction mixture which contains 5 units of EcoRI in buffer for use with EcoRI. Then the reaction mixture was separated on agarose electrophoresis, and the expected bands for DNA (at 0.33 kb) were checked by ethidium bromide staining. The results showed that nine of the clones gave the desired band. The plasmids extracted from these nine clones were doubly digested with the use of PvuII and HindIII. Then the orientation of the inserted fragments was identified. It was found that eight of the clones had the inserts with the correct orientation. Of these eight clones, the plasmids from five clones were doubly digested with the use of XbaI and HindIII, and the DNA that contained the inserted fragments were removed, subcloned into the phages M13mp18 and mp19. The base sequences were analyzed by the dideoxy method. Three of the clones were found to contain the desired sequence. The recombinant plasmids obtained in this way were named pTF101.

(1-7) Purification of plasmids

The pTF101 obtained as described above in section (1-6) was used to transform *Escherichia coli* cells (SB221/pTF 101) and such transformed cells were cultured in 5 ml of L-broth overnight with agitation at 37° C. The culture was transferred to 500 ml of the same culture broth and culture was continued until the absorbance at 660 nm reached 0.6, at which time 170 μg/ml chloramphenicol was added, and cultured was continued once more for 10–12 hours. The culture broth was centrifuged for 10 minutes at 5000 rpm, and the cell pellet was washed in STE (10 mM Tris-HCl, pH 8, 100 mM NaCl, and 1 mM EDTA), and centrifuged again in the same way in order to obtain the cell pellet. The pellet was suspended in 10 ml of the solution A, and kept at room temperature for 5 minutes before 20 ml of the solution B was added with rapid stirring, and the suspension was left for 5 minutes at 0° C. To this suspension, 15 ml of 3 M potassium acetate was added with rapid stirring, and the suspension was left at 0° C. for 10 minutes. The mixture was centrifuged for 60 minutes at 8000 rpm and the supernatant was obtained, to which 27 ml (0.6 volume) of isopropyl alcohol was added, and the mixture was left at room temperature for 15 minutes. This mixture was centrifuged and the precipitate was collected and washed in 80% ethanol. The ethanol and water in the resulting mixture was removed under reduced pressure and the residue was dried. This residue was dissolved in 4 ml of TE and to this solution, 4.75 g of cesium chloride was added, followed by the addition of 5 mg/ml ethidium bromide in the volume of 420 μl; the mixture was left for 30 minutes at 0° C. The mixture was then centrifuged for 10 minutes at 8000 rpm, and the supernatant was put into a Bechman Quick-seal tube and ultracentrifuged at 55000 rpm overnight. Then, under ultraviolet light, plasmid bands were removed by the use of a syringe. The resulting mixture was extracted seven times in equal volumes of isopropyl alcohol and the remaining ethidium bromide was removed, after which ethanol precipitation was done twice, and then the remaining mixture was washed in 80% ethanol, dried under reduced pressures, and dissolved in a drop of TE (yield, 760 μg).

EXAMPLE 2

Cloning of the cDNA fragment that codes for $Ala^{1235}$-$Met^{1517}$ (283 amino acid residues) of fibronectin (see FIG. 2):

FIG. 2 is a diagram of the processes involved in the construction of an expression plasmid which carries the DNA sequence which codes for the polypeptide which includes the $Ala^{1235}$-$Met^{1517}$ sequence of fibronectin.

First, 50 μg of the plasmid pLF5 was put into 200 μl of a reaction mixture containing 200 units of EcoRI methylase in a buffer for use with EcoRI methylase (100 mM Tris-HCl, pH 8.0, 2 mM DTT, 10 mM EDTA, and 80 μM S-adenosylmethionine), and the mixture was incubated for 60 minutes at 37° C. to bring about protection of the EcoRI sites. Then the reaction was stopped by being heated at 65° C. for 20 minutes, and 96 units of PvuII in buffer for use with PvuII was added; 300 μl of the reaction mixture was incubated for 60 minutes at 37° C. This mixture was separated by agarose electrophoresis, and the slice of gel containing 0.60 kb band was cut out. This slice was put into a dialysis tube that contained elution buffer (5 mM Tris-acetate buffer, pH 8.0, and 1 mM EDTA), and elution by electrophoresis occurred in the same buffer, by which means the DNA was eluted. The elution fluid was extracted twice with phenol, and a 1/10 volume of 3 M sodium acetate was added, followed by the addition of two volumes of ethanol, and ethanol precipitation was conducted twice. Then the resulting mixture was washed in 80% ethanol, dried, and dissolved in a small amount of TE (yield, 1.2 μg).

Also, 140 μg of the plasmid pTF101 obtained in Example 1 was put into 200 μl of a reaction solution containing 144 units of PvuII, and the mixture was incubated for 60 minutes at 37° C. Then 150 units of EcoRI was added, and the reaction solution brought to 240 μl, and incubated for 60 minutes at 37° C. The result was separated by polyacrylamide electrophoresis, and the bands at 0.25 kb were cut out. The DNA was extracted from these bands of gel as described above, and the DNA was collected by ethanol precipitation (yield, 0.4 μg). Then 1.25 μg of the 0.6-kb fragments obtained here and 0.4 μg of the 0.25-kb fragments were put into a ligation buffer which contains 2.8 units of T4 DNA ligase, 0.5 mM ATP, and 10 mM DTT in 50 μl, and the mixture was incubated for 30 minutes at 16° C. Then 92 pmol of phosphorylated linker (pCCGAATTGG) and 1.4 units of T4 DNA ligase were added to the reaction mixture, which was brought to 70 μl and incubated overnight at 10° C. The reaction was stopped by heating at 65° C. for 10 minutes, and the buffer was modified to be suitable for EcoRI; 30 units of EcoRI was added, and reaction was allowed to take place for 60 minutes at 37° C. Then the reaction mixture was separated by agarose electrophoresis, and the 0.86-kb bands were cut out. The DNA in the bands was obtained by the method described above (yield, about 25 ng). Then 20 ng of the 0.86-kb fragments were cleaved with EcoRI, and put into a ligation buffer which contains 0.1 μg of dephosphorylated vector pIN-III-OMPA-1, 2.8 units of T4DNA ligase, 0.5 mM ATP, and 10 mM DTT in a total volume of 20 μ; the mixture was incubated for 10 hours at 16° C. and half of the reaction was used to transform Escherichia coli SB 221 cells by the method described above. Of the transformants obtained, 48 of the clones were analysed for plasmids by the methods described above, and it was found that the plasmids included the desired fragments in six of the clones. These six plasmids were digested with m/ HI, and the fragments which were produced were analysed. Five of the clones contained the desired fragments inserted in the correct orientation. Three of these five clones were studied for their base sequence. One of the clones was found to have the correct base sequence. This recombinant plasmid was named pTF301, and the cells of Escherichia coli SB221 that carry this plasmid were designated SB221/pTF301. Next, a 1.8-kb EcoRI-SalI fragment was removed from PTF301, and these were joined with the EcoRI-SalI site of pUC18; the recombinant plasmid obtained was named pTF1409, and the Escherichia coli HB101 cells that carry the plasmid were designated HB101/pTF1409. The strain was deposited on Nov. 19, 1987 at the Fermentation Research Institute of the Agency of Industrial Science and Technology, 1-3, Higashi 1-chome Tsukuba-shi Ibaraki-ken 305, Japan, under FERM BP-1939.

EXAMPLE 3

Cloning of the cDNA fragment which codes for Gly$^{1014}$-Met$^{1517}$ (504 amino acid residues) of fibronectin (see FIG. 3):

FIG. 3 is a diagram of the processes involved in the construction of an expression plasmid which carries the DNA sequence which codes for the polypeptide including the Gly$^{1014}$-Met$^{1517}$ sequence of fibronectin.

(3-1) Synthesis of the primer-extended cDNA

The 17-base synthetic primer (5'pGTCTCCCACT-GAAGTGC3') that is the complementary sequence to the mRNA of fibronectin was prepared following the method described above (1-2). This synthetic primer was used to synthesize cDNA from poly(A$^+$)RNA of human origin (from Clontec Laboratories, Inc.).

In the synthesis of cDNA, reagents from the cDNA synthesis system of Amersham were used. These included 4 μl of 5x buffer for the synthesis of the first strand, 1 μl of sodium pyrophosphate solution, 1 μl of ribonuclease inhibitor (20 units), 2 μl of a mixture of deoxyribonucleotide triphosphate (10 mM), 1 μl of synthetic DNA primer (0.1 μg), 5 μCi of [α-$^{32}$P] dCTP, and 1 μl of poly(A$^+$)RNA (1 μg), which reagents were added in this order to a cooled Eppendorf tube, the contents of which were gently mixed. Then 20 units of reverse transcriptase (1 μg) and distilled water were added to the tube to bring the total volume to 20 μl, and the contents were gently mixed. The mixture was incubated for 50 minutes at 42° C. The tube was returned to an ice-bath and the following were added, in this order: 37.5 μl of a buffer for use in synthesis of the second strand, 50 μCi of [α-$^{32}$P]dCTP (5 μl), 0.8 unit of ribonuclease H from Escherichia coli (1 μl), 23 units of Escherichia coli DNA polymerase 1 (3.5 μl), land 33 μl of water. The contents of the tube were gently mixed. The tube was incubated first for 60 minutes at 12° C., then for 60 minutes at 22° C., and then for 10 minutes at 70° C., before being returned to an ice-bath. Then 2.0 units (0.5 μl) of T4 DNA polymerase was added. After gentle mixing of the contents, the tube was incubated for 10 minutes at 37° C. Then the reaction was stopped by the addition of 10 μl of 0.25 M EDTA (pH 8.0) and 10 μl of 10% SDS. Phenol extraction was done twice, and then an equal volume of 4 M ammonium acetate was added, followed by the addition of two volumes of cooled ethanol. The mixture was left for 15 minutes in dry ice, and then returned to room temperature. The mixture was centrifuged for 10 minutes and the supernatant removed. The pellet was dissolved in 50 μl of TE, and ethanol precipitation was repeated once more. The precipitate was washed in 200 μl of cooled ethanol, dried, and dissolved in a small amount of TE.

(3-2) Ligation of cDNA with the λgt 10 phage vector and in vitro packaging

The cDNA obtained in section (3-1) above was put into 16.6 μl of a reaction mixture which contains 0.5 μg of EcoRI linker (d[pGGAATTCC]), ligation buffer and 2.8 units of T4 DNA ligase, and the mixture was incubated overnight at 15° C. Then the reaction was stopped by treatment for 10 minutes at 70° C. The buffer was changed to one suitable for the reaction of EcoRI, and 50 units of EcoRI was added; the total volume brought to 100 μl before incubation for 2 hours at 37° C. Then the reaction was stopped by treatment for 10 minutes at 70° C. The entire mixture was put on a Sephadex G-50 column (1 ml) and the column was eluted with STE buffer (100 mM NaCl, 10 mM Tris-HCl, and 1 mM EDTA, pH 8.0). The free linker was removed in this way. Then the cDNA fraction was dialyzed against 10 mM Tris-HCl (pH 8.0) and 0.1 mM EDTA, after which it was lyophilized. To the resultant substance were added 333 mM NaCl and 10 mM $MgCl_2$, and the mixture was made to 4.5 μl, after which 0.5 μl (0.25 μg) of λgt 10/EcoRI Arms (Amersham) was added, followed by 5 μl of solution B from a DNA ligation kit (Takara Shuzo). The mixture was incubated for 10 minutes at 26° C., and the reaction was stopped by treatment for 10 minutes at 70° C. This allows an in vitro packaging reaction to take place. Into 4 μl of reaction fluid, two kinds of packaging extracts (Stratagene) were gently mixed in and incubation follows for 2 hours at 22° C., during which time phage particles were formed. Then 500 μl of SM buffer (100 mM NaCl, 8 mM $MgSO_4$, 50 mM Tris-HCl, pH 7.5, and 0.01% gelatin) were added with 20 μl of chloroform, and lthe mixture was kept at 4° C.

(3-3) Plaque hybridization:

First, 100 μl of the mixture prepared above was added to 200 μl of a Escherichia coli NM 514 culture which had been cultured overnight on L-broth plus 4% maltose, and this was incubated for 15 minutes at 37° C. Then, 4 ml of L soft agar medium (L-broth plus 8% agar) heated to 42° C. was added before it was overlayed on top of 20 ml of L-agar plate. This clulture was incubated overnight at 37° C. and the nylon filters (Hybond N, Amersham) were placed on top of the plates for 30 seconds. The filters were placed for 5 minutes on top of thick filter paper that had been saturated with denaturing solution (0.5 M NaCl and 1.5 M NaCl); then, they were placed for 5 minutes on top of thick filter paper that had been saturated with neutralizing solution (0.5 M Tris-HCl, pH 7.0, and 1.5 M NaCl). Next, the filters were washed with 2x SSC (0.3 M NaCl and 30 mM sodium citrate, pH 7.0) and dried. They were fixed with ultraviolet ;illumination at 300 nm for 5 minutes, and used as replica filters. Separately, a probe for use in hybridization was prepared. First, 4 μg of the plasmid pLF5 was digested with 12 units of PvuII, and next with 15 units of EcoRI, and 100 ng of the resulting 0.43-kb fragment was obtained by agarose electrophoresis. The fragment obtained was labelled with $^{32}P$ by use of the multiprime DNA labelling system of Amersham according to the attached protocol. The labelled probe thus obtained had an activity of $5.5 \times 10^7$ cpm per 60 μl. The replica filters mentioned above were put into 15 ml of a solution which contains 6x SSC, 5x Denhardt (BSA, polyvinylpyrrolidone, and 0.1% Ficoll), 0.5% SDS, and 80 μg/ml salmon sperm DNA, and the whole was incubated for 4 hours at 65° C., during which time prehybridization occurred. Next,labelled probe ($2.75 \times 10^7$ cpm) which had been heat-denatured was added to the mixture, and hybridization was allowed to take place overnight under the same conditions. The filters were washed twice in 2x SSC and 0.1% SDS for 15 minutes at 65° C.; and then washing was done twice in 0.2x SSC and 0.1% SDS for 15 minutes at 65° C. 2x SSC was used for a brief rise, and autoradiography was was conducted. The result was the finding of a radioactive signal among 250 of the $4 \times 10^3$ plaques.

(3-4) Preparation of phage, DNA and analysis of inserted fragments

Phage clones which gave a positive signal were suspended in 1 ml of SM buffer, and 250 μl of this suspension was added to 0.5 ml of a culture of Escherichia coli NM514 cells which had lbeen cultured overnight. The mixture was incubated for 15 minutes at 37° C, and the phages allowed to attach; 5 ml of L-broth containing 10 mM $MgCl_2$ was added, and culture was carried out for 4.5 hours at 37° C. with shaking. To the culture was added 50 μl of chloroform, and shaking was continued for 10 minutes. Then the culture was centrifuged and the supernatant (the phage lysate) was obtained. Then, to the phage lysate, 20 μg of DNase I and 10 μg of RNase A were added, and the mixture was inculated for 3 minutes at 37° C. Then 0.29 g of NaCl was added together with 0.55 g of PEG 6000, and the mixture was incubated over ice for 2 hours. The pellet was obtained from centrifugation of this mixture, and suspended in 400 μl of TE. Phenol extraction was conducted twice, phenol/chloroform extraction was conducted once, and chloroform extraction was conducted once, after which ethanol precipitation was performed. In this way, phage DNA was obtained. The phage DNA was dissolved in 20 μl of TE, and put into 30 μl of a reaction mixture containing 20 units of EcoRI; the mixture was incubated for 2 hours at 37° C. The inserted fragments were analyzed by the use of agarose electrophoresis. The results were that, of the 24 clones, one clone was found to have a 1.1-kb inserted fragment. This 1.1-kb fragment was subcloned in the plasmid pUC118, and the recombinant plasmid obtained was designated pUFN74. This plasmid was used in the identification by the dideoxy method of the base sequence of the inserted fragment. It was found that this fragment was the cDNA of fibronectin (EMBO Journal, 4 [1985], 1755–1759), starting from the G in the 2990th position to the A in the 4105th position. However, the C in the 3018th position, the C in the 3063rd position, and the C in the 3216th position were replaced by A, A, and T, respectively; however, there was no change in the amino acids coded for.

(3-5) Preparation of EcoO109BamHI fragment of pUFN74

Per 40 μg of pUFN74, 200 units of EcoO109 was added, and in a reaction mixture of 400 μl, these were incubated for 2 hours at 37° C. Then ethanol precipitation was used to collect the DNA. Half of the DNA obtained was put into 200 μl of a reaction mixture which contains 7 mM Tris-HCl, pH 7.5, 1 mM EDTA, 20 mM NaCl, 7 mM $MgCl_2$, 20 μM dATP, 20 μM dGTP, 20 μM dCTP, 20 μM dTTP, and 2 units of Klenow fragment. This mixture was incubated for 20 minutes at room temperature. Then the reaction was stopped by treatment for 10 minutes at 65° C., and the reaction mixture was given the compositon of ligation buffer followed by the addition of 2.5 nmol of EcoRI linker (d[pCCGAATTCGG]) and 2.8 units of T4 DNA ligase. This mixture was incubated overnight at 13° C. The reaction was stopped by heating of the mixture. This was put into 400 μl of a reaction mixture containing 60 units of BamHI and 50 units of EcoRI, and the whole was incubated for 2 hours at 37° C. Then a 1.0-kb fragment was obtained by agarose electrophoresis; the yield was 0.2 μg.

(3-6) Preparation of BamHI-HindIII fragment of pTF301

First, 200 units of EcoRI methylase was added to 50 μg of pTF301, and this was made to 200 μl; the reaction mixture was incubated for 1 hour at 37° C. Then the mixture was treated for 20 minutes at 65° C., and made to 400 μl. To the reaction mixture were added 60 units of BamHI and 60 units of HindIII. The mixture was incubated for 2 hours at 37° C. Then a 0.5-kb fragment was obtained by agarose electrophoresis; the yield was 0.1 μg.

(3-7) Construction and cloning of cDNA fragments which code for $Gly^{1014}$-$Met^{1517}$ (504 amino acid residues)

First, 0.2 μg of the 1.0-kb fragment obtained in section (3-5) above and 0.1 μg of the 0.5-kb fragment obtained in section (3-6) above were put into 100 μl of a ligation buffer, to which 2.8 units of T4 DNA ligase was added, and the whole was incubated overnight at 16° C. before being heat-treated at 70° C. for 10 minutes to stop the reaction. The reaction mixture was made into a buffer for the use of HindIII, and 100 μl of the reaction mixture containing 12 units of HindIII was incubated for 2 hours at 37° C. Then, the buffer was made into a buffer for the use of EcoRI, and 10 units of EcoRI was added, and the whole was incubated for 2 hours at 37° C. The reaction was stopped by the addition of heat. Then 20 μl of this reaction mix- ture was added to 30 μl of a reaction mixture containing 0.16 μg of dephosphorylated plasmid pIN-III-ompA-1 treated with EcoRI-HindIII and 2.8 units of T4 DNA ligase. This mixture was incubated overnight at 16° C. Half of the reaction mixture was used for the transformation of Escherichia coli HB101 cells. Of the transformants obtained, 12 clones were studied for the inserted fragments that they contained. Five of the clones contained 1.5-kb fragment. Their base sequences were identified by the dideoxy method, and a plasmid that contained the cDNA that codes for the $Gly^{1014}$-$Met^{1517}$ sequence of fibronectin was found. This plasmid was designated pTF1101.

EXAMPLE 4

Removal of an extra sequence by the use of site-specific mutagenesis (see FIG. 4):

FIG. 4-1 is a diagram that shows the DNA sequence of pTF101 and the amino acid sequence both before and after removal of the extra sequence, and FIG. 4-2 is a diagram of the processes involved in the removal of an extra DNA sequence from pTF101 by use of site-specific mutagenesis.

When the cDNA fragments that have been inserted in pTF101 or pTF301 are expressed, a peptide that is added to the three amino acids originating from the vector at the N-terminus other than the signal peptide is produced. The signal peptide can be removed by the signal peptidase of the host, but the amino acids attached to the N-terminal side cannot be removed as is. Thus, removal of these three amino acids was tried by bringing about site-specific mutagenesis of the 9-bp sequence that codes for the amino acids. The method used was that of Inoue et al. (*Proceedings of the National Academy of Sciences, U.S.A.*, 79 (1982), 3438-3441; FIGS. 4-1 and -2).

First, 5 μg of pTF101 was cleaved with PstI, and Klenow fragment was used to change the cohesive ends to blunt ends. This linealized plasmid with blunt ends was collected by ethanol precipitation and dissolved in 40 μl of TE (fragment 1). Separately, 5 μg of pTF101 was cleaved with XbaI and HindIII, to remove the inserted fragment followed by 5% acrylamide electrophoresis. This was dissolved in 40 μl of TE (fragment 2). Also, an oligonucleotide primer (dGTAGCGCA . . . ) for use in the insertion of mutations was synthesized, and disolved in TE at the 7 concentration of 20 pmol/μl. Then, 25 μl of this solution was added to 50 μl of a kination buffer which contains 5 units of PNK and 0.03 mM ATP, and the whole was incubated for 60 minutes at 37° C. in order to phosphorylate the 5' termini. Then 0.3 μg of fragment 1, 0.28 μg of fragment 2, and 75 pmol of oligonucleotide primer were put into 35 μl of a reaction mixture containing a buffer for both polymerase and ligase (100 mM NaCl, 6.5 mM Tris-HCl, pH 7.5, 8 mM $MgCl_2$, and 1 mM mercaptoethanol), and the mixture was boiled for 3 minutes before being incubated for 30 minutes at 30° C. Then incubation continued at 4° C. for 30 minutes. One portion of the incubation mixture was separated by agarose electrophoresis, and heteroduplex chains were found. Next, 10 μl of the reaction mixture was put into 20 ml of a reaction mixture that contained dATP, dGTP, dCTP, and dTTP, all 0.5 mM, and 1 mM ATP, 2 units of Klenow fragment, and 1 unit of T4 DNA ligase; the mixture was incubated overnight at 12° C. The reaction mixture was used to transform cells of Escherichia coli HB101. Of the 200 colonies obtained, the plasmids of 100 colonies were prepared by the conventional method, and PstI-EcoRI fragments produced were studied. Of the two EcoRI sites, a clone which had lost one site was selected. Five clones had the desired plasmids. Of these, a XbaI-HindIII fragment of the plasmid from one clone was subcloned into the M13mp18 and the M13mp19, and the base sequence was analized by the dideoxy method. It was confirmed that the 9 bp of vector origin had been removed. The plasmid obtained in this way was designated pTF201. In exactly the same way as for pTF301, the 9 bp of vector origin was removed from the other plasmid, which was designated pTF901.

EXAMPLE 5

Production and preparation of the $Ile^{1410}$-$Met^{1515}$ polypeptide (108 amino acid residues) of fibronectin:

Cells of Escherichia coli HB101/pTF201 that carried the plasmid pTF201 were used to inoculate into two test tubes that contained 5 ml of L-broth that had added to it 50 μg/ml ampicillin, and the test tube were cultured overnight at 37° C. These were used separately to inoculate 2-1 Erlenmeyer flask that contained 500 ml of the same broth, and culture was continued until the absorbance at 660 nm reached 0.3. At this point, 2 mM of isopropyl-β-thiogalactoside (IPTG) was added, and the cells were harvested 2 hours later. Some of the cells were used for immunoblotting. The whole-cell protein was separated by SDS-polyacrylamide electrophoresis (SDS-PAGE), and the electrophoretic pattern was transferred to a nitrocellulose membrane, after which an anti-fibronectin monoclonal antibody, FM-10 (Takara Shuzo), was used to identify the cell-spreading domain of fibronectin specifically. Next, a second antibody labelled with peroxidase was used. The bound second antibody gave rise to color in the presence of hydrogen peroxide and 4-chloronaphthol, and the production of the desired peptide could be verified in this way. Next, the whole-cell pellet was suspended in a solution containing 10 mM Tris-HCl, pH 7.5, 5 mM EDTA, and 5 mM mercaptoethanol, and ultrasonication of the suspension was conducted. Then the sonicate was centrifuged for 30 minutes at 12000 rpm. Twenty milliliters of supernatant was obtained. This supernatant was dialysed against a 20 mM Tris-HCl (pH 7.5) buffer, and then passed through a Sepharose 4B column (8 ml) which had the antifibronentin antibody FN-10 bound to it. The column was washed with buffer A (20 mM Tris-HCl, pH 8.0, and 0.15 M KCl), and washed again with buffer B (20 mM Tris-HCl, pH 6.4, and 0.15 M KCl). Finally, an eluent buffer (50 mM glycine.HCl, pH 2.3, and 0.20 M KCl) was used for elution. The fractions of the desired polypeptide were collected. Next, these fractions were put on a Mono S HR 5/5 column (Pharmacia) and eluted with the use of a concentration gradient of NaCl in 20 mM acetate buffer; upon electrophoresis, 4 mg of almost pure polypeptide was obtained. The sequence of the 10 amino acid residues on the N-terminal side of the polypeptide obtained was identified. It was the same as the sequence of $Ile^{1410}$-$Val^{1419}$ of fibronectin. The amino acid composition was analyzed, and the results were the same as the theoretical values. However, on SDS-PAGE, the desired band was found in the vicinity of the molecular weight of about 14000, which was a higher value than the predicted molecular weight of 11500. This may have been because of the high proportion of proliness in the peptide (9 residues among the 108 residues). In fact, when the proportion of proliness in a protein is high, it is known that by SDS-PAGE, the molecular weight 1- will be higher than predicted (*Molecular and Cellular Biology*, 4 [1984], 2486).

EXAMPLE 6

Production and purification of a peptide which includes the $Ala^{1235}$-$Met^{1517}$ polypeptide (283 amino acid residues) of fibronectin:

Cells of *Escherichia coli* HB101/pTF901 which carries the plasmid pTF901 were cultured by the same method as in Example 5, and a peptide was purified in the same way from 2 liters of culture broth, and found to be almost pure by electrophoresis; the yield was about 400 µg. The amino acid sequence on the N-terminal side of this polypeptide was studied, and it was found that one portion of the signal peptide that originated from the vector (Ala-Gly-Phe-Ala-Val-Ala-Gln-Ala) was attached.

Next, cells of *Escherichia coli* HB101/pTF1409 that carried plasmid pTF1409 were cultured in the same way, and about 600 µg of polypeptide was purified from 2 liters of culture broth. The amino acid sequence of the N-terminal side of this polypeptide was studied, and it was found that an amino acid sequence (Met-Thr-Met-Ile-Thr-Asn-Ser) that originated from the vector was attached.

EXAMPLE 7

Production and preparation of polypeptide which contains the $Gly^{1014}$-$Met^{1517}$ sequence (504 amino acid residues) of fibronectin:

Cells of *Escherichia coli* HB101/pTF1101 which carries plasmid pTF1101 were used, and 1 liter of culture was obtained in the same way as in Example 5. The cells were lysed by ultrasonication, and dialyzed. After centrifugation, the supernatant was put on a Sepharose 4B column bound with antibody, and 600 µg of purified polypeptide was obtained judged by electrophoresis. The amino acid sequence of the N-terminal side of this polypeptide was studied, and it was found that the signal peptide and a sequence of Ala-Asn-Ser both originating from the vector were attached.

EXAMPLE 8

Measurement of cell-spreading activity:

The polypeptides obtained in Examples 5-7 above were used for measurement of their cell-spreading activities. The method used was that of Ruoslahti et al. (*Methods in Enzymology*, 82 [1981], 803-831). As the positive control, fibronectin of human origin was used. The sample was diluted stepwise in 0.1 M $NaHCO_3$, and 50 µl was injected into the wells of a 96-well microplate, which was then incubated for 1 hour at 37° C. to allow the sample to adhere to the plate. Next, phosphate-buffered saline (PBS) was used to wash the plate twice, and 100 µl of 1% BSA was added to each well. The plate was blocked by incubation for 1 hour at 37° C. The plate was then washed twice with PBS. Then normal rat kidney (NRK-49F) cells suspended in Eagle's minimum essential medium (MEM) to the concentration of $10^6$ cells were injected at the volume of 100 µl/well, and the plate was incubated for 2-3 hours at 37° C. Morphological changes in the cells were looked for under a microscope, and the minimum dose of the polypeptides that caused cell-spreading activity was found. The results are shown below in Table 1.

TABLE 1

| Polypeptide | Minimum dose with cell-spreading activity | |
|---|---|---|
| | ug/well | (pmol/well) |
| $Ile^{1410}$—$Met^{1517}$ | >50 | (>4400) |
| $Ala^{1235}$—$Met^{1517}$ | 0.19 | (6.1) |
| $Gly^{1014}$—$Met^{1517}$ | 0.16 | (2.8) |
| Fibronectin | 1.50 | (3.75) |

EXAMPLE 9

Cloning and expression of the cDNA which codes for a polypeptide to which a cystein residue is attached to the C-terminus (see FIG. 5):

FIG. 5 is a diagram of the processes involved in the construction of an expression plasmid which carries the DNA sequence which codes for a polypeptide with a cystein residue attached to the C-terminus.

The XbaI-HindIII fragment (0.44 kb) were removed from the plasmid pTF201 obtained in Example 4, and cleaved with FokI, giving a XbaI-FokI fragment (175 bp) and a FokI-FokI fragment (203 bP).

Separately, synthetic DNA to which a cystein codon (TGC) was attached in front of the stop codon of the FokI-EcoRI fragment at their C-terminal side was prepared, and a duplex chain was obtained after phosphorylation. Fragments obtained in this way (XbaI-FokI, FokI-FokI, and FokI-EcoRI) were joined with the use of DNA ligase to vectors of pTF201 from which the XbaI-EcoRI fragments had been removed, and cells of *Escherichia coli* HB101 were transformed by the use of the vector. Plasmids were purified from the transformants obtained, and its XbaI-EcoRI fragment was subcloned into M13mp18. The base sequence of the resultant insert was studied by the dideoxy method, and it was found that the sequence TGC that corresponds to a cystein on the 3'-end was attached. In this way, a plasmid that carried cDNA that codes for a polypeptide that has attached to the C-terminus of the sequence Ile¹⁴¹⁰-Met¹⁵¹⁷ a cystein residue was obtained. The plasmid was named pTF-1201.

Next, the PvuII-HindIII fragment was removed from pTF1201, and the XbaI-PvuII fragment was removed from the pTF901 obtained in Example 4, and these fragments were purified. The fragments were then joined by the use of DNA ligase to a vector from of pTF901 from which the XbaI-HindIII fragments had been removed, and the vector was used to transform cells of *Escherichia coli* HB101. The plasmids of the transformants obtained were extracted, and the insertion fragment was subcloned into M13mp18. Then the base sequence of the insert obtained was studied by the dideoxy method. It was found that the sequence TGC that corresponds to the cystein residue of the 3'-end was attached. In this way, a plasmid that carried the cDNA that codes for a polypeptide of the sequence Ala¹²³⁵-Met¹⁵¹⁷ that has a cystein residue at its C-terminus was obtained, and the plasmid was designated pTF1501. pTF1501 was cultured in the same way as in Example 5, and purification gave 500 μg of purified polypeptide from 1 liter of culture broth. The amino acid sequence of this polypeptide was analyzed, and it was found that there was one cystein residue in the molecule, in agreement with the theoretical value.

As has been explained above in detail, this invention provides a polypeptide which has cell-spreading activity essentially the same as that of fibronectin, and also provides a method for its preparation by the use of genetic engineering.

What we claim is:

1. A polypeptide with cell-spreading activity which has the following amino acid sequence:

Ala Val Pro Pro Pro Thr Asp Leu Arg Phe

Thr Asn Ile Gly Pro Asp Thr Met Arg Val

Thr Trp Ala Pro Pro Pro Ser Ile Asp Leu

Thr Asn Phe Leu Val Arg Tyr Ser Pro Val

-continued

Lys Asn Glu Glu Asp Val Ala Glu Leu Ser

Ile Ser Pro Ser Asp Asn Ala Val Val Leu

Thr Asn Leu Leu Pro Gly Thr Glu Tyr Val

Val Ser Val Ser Ser Val Tyr Gly Gln His

Glu Ser Thr Pro Leu Arg Gly Arg Gln Lys

Thr Gly Leu Asp Ser Pro Thr Gly Ile Asp

Phe Ser Asp Ile Thr Asn Ala Ser Phe Thr

Val His Trp Ile Ala Pro Arg Ala Thr Ile

Thr Gly Tyr Arg Ile Arg His His Pro Glu

His Phe Ser Gly Arg Pro Arg Glu Asp Arg

Val Pro His Ser Arg Asn Ser Ile Thr Leu

Thr Asn Leu Thr Pro Gly Thr Glu Tyr Val

Val Ser Ile Val Ala Leu Asn Gly Arg Glu

Glu Ser Pro Leu Leu Ile Gly Gln Gln Ser

Thr Val Ser Asp Val Pro Arg Asp Leu Glu

Val Val Ala Ala Thr Pro Thr Ser Leu Leu

Ile Ser Trp Asp Ile Thr Tyr Gly Glu Thr

Gly Gly Asn Ser Pro Val Gln Glu Phe Thr

Val Pro Gly Ser Lys Ser Thr Ala Thr Ile

Ser Gly Leu Lys Pro Gly Val Asp Tyr Thr

Ile Thr Val Tyr Ala Val Thr Gly Arg Gly

Asp Ser Pro Ala Ser Ser Lys Pro Ile Ser

Ile Asn Tyr Arg Thr Glu Ile Asp Lys Pro

Ser Gln Met

* * * * *

UNITED STATES PATENT AND TRADEMARK OFFICE
CERTIFICATE OF CORRECTION

PATENT NO. : 5,049,658

DATED : September 17, 1991

INVENTOR(S) : Fusao KIMIZUKA et al

It is certified that error appears in the above-identified patent and that said Letters Patent is hereby corrected as shown below:

Column 18, eighth line from the bottom, after "Asp", insert -- Ala Pro Ala Val Thr Val Arg Tyr Tyr Arg --.

Signed and Sealed this

First Day of June, 1993

Attest:

MICHAEL K. KIRK

Attesting Officer

Acting Commissioner of Patents and Trademarks